United States Patent [19]
Kotula et al.

[11] Patent Number: 5,846,261
[45] Date of Patent: *Dec. 8, 1998

[54] PERCUTANEOUS CATHETER DIRECTED OCCLUSION DEVICES

[75] Inventors: Frank Kotula, Maple Grove; Kurt Amplatz, St. Paul, both of Minn.

[73] Assignee: AGA Medical Corp., Golden Valley, Minn.

[ * ] Notice: The term of this patent shall not extend beyond the expiration date of Pat. No. 5,725,552.

[21] Appl. No.: 925,935

[22] Filed: Sep. 8, 1997

Related U.S. Application Data

[63] Continuation-in-part of Ser. No. 647,712, May 14, 1996, Pat. No. 5,725,552, which is a continuation-in-part of Ser. No. 272,335, Jul. 8, 1994.

[51] Int. Cl.⁶ .................................................. A61B 17/08
[52] U.S. Cl. .......................................................... 606/213
[58] Field of Search ..................................... 606/213, 215, 606/216, 217, 151, 153, 191–198, 199, 200; 604/167, 281; 600/32; 128/899

[56] References Cited

U.S. PATENT DOCUMENTS

| | | |
|---|---|---|
| 3,874,388 | 4/1975 | King et al. . |
| 4,007,743 | 2/1977 | Blake . |
| 4,503,569 | 3/1985 | Dotter . |
| 4,553,545 | 11/1985 | Maass et al. . |
| 4,572,186 | 2/1986 | Gould et al. . |
| 4,619,346 | 10/1986 | Molgaard-Nielsen et al. ......... 128/1 R |
| 4,649,922 | 3/1987 | Wiktor . |
| 4,655,772 | 4/1987 | De Liotta et al. . |
| 4,665,906 | 5/1987 | Jervis ................................. 128/92 YN |
| 4,681,110 | 7/1987 | Wiktor . |
| 4,690,684 | 9/1987 | McGreevy et al. . |
| 4,699,611 | 10/1987 | Bowden . |
| 4,723,549 | 2/1988 | Wholey et al. . |
| 4,732,152 | 3/1988 | Wallstén et al. . |

(List continued on next page.)

FOREIGN PATENT DOCUMENTS

| | | |
|---|---|---|
| 489252 | 10/1976 | Australia . |
| 0541063A2 | 12/1993 | European Pat. Off. . |
| 93/10714 | 6/1993 | WIPO . |

OTHER PUBLICATIONS

"Catheter Closure of the Ductus Arteriosus" from Transcatheter Therapy in Pediatric Cardiology–1993 pp. 321–333.

"Transcatheter Closure of Atrial Septal Defects" from Transcatheter Therapy in Pediatric Cardiology–1993–pp. 335–348.

"Transcatheter Closure of Heart Defects: Rule of Buttoned Devices" from Transcatheter Therapy in Pediatric Cardiology–1993 pp. 349–369.

Palmaz, et al. "Atherosclerotic Rabbit Aortas: Expandable Intraluminal Grafting", Radiology 1986; 160; 723–726.

Rosseau, et al. "Self–expanding Endovascular Prosthesis: An Experimental Study", Radiology 1987; 164; 709–714.

(List continued on next page.)

Primary Examiner—Michael Buiz
Assistant Examiner—Vikki Trinh
Attorney, Agent, or Firm—Haugen and Nikolai, P.A.

[57] ABSTRACT

A collapsible medical device and associated methods for occluding an abnormal opening in, for example, a body organ, wherein the medical device is shaped from a heat treatable metal fabric. The metal fabric is formed from a plurality of metal strands and is heat treated within a mold in order to substantially set a desired shape of the device. The medical device includes a fastener for attaching to the end of a guide wire or delivery catheter, wherein the shape of the medical device is formed such that the fastener is attached to the metal fabric within a recess formed in the shape of the medical device. A medical device having a preselected shape is delivered through a catheter or the like for deployment in a desired channel or opening in a patient's body. The medical device may be shaped, for example, to occlude an ASD, PDA, or a VSD.

18 Claims, 10 Drawing Sheets

U.S. PATENT DOCUMENTS

| | | |
|---|---|---|
| 4,733,665 | 3/1988 | Palmaz . |
| 4,793,348 | 12/1988 | Palmaz . |
| 4,794,928 | 1/1989 | Kletschka . |
| 4,800,882 | 1/1989 | Gianturco . |
| 4,830,003 | 5/1989 | Wolff et al. . |
| 4,832,055 | 5/1989 | Palestrant ................................ 128/899 |
| 4,836,204 | 6/1989 | Landymore et al. . |
| 4,848,343 | 7/1989 | Wallstén et al. . |
| 4,856,516 | 8/1989 | Hillstead . |
| 4,886,062 | 12/1989 | Wiktor . |
| 4,917,089 | 4/1990 | Sideris . |
| 4,921,484 | 5/1990 | Hillstead . |
| 4,991,602 | 2/1991 | Amplatz et al. . |
| 5,016,808 | 5/1991 | Heil, Jr. et al. . |
| 5,034,001 | 7/1991 | Garrison et al. . |
| 5,064,435 | 11/1991 | Porter . |
| 5,067,489 | 11/1991 | Lind . |
| 5,067,957 | 11/1991 | Jervis ...................................... 606/108 |
| 5,108,420 | 4/1992 | Marks . |
| 5,171,259 | 12/1992 | Inoue . |
| 5,190,546 | 3/1993 | Jervis ........................................ 606/78 |
| 5,246,445 | 9/1993 | Yachia et al. . |
| 5,256,146 | 10/1993 | Ensminger et al. . |
| 5,334,217 | 8/1994 | Das . |
| 5,382,259 | 1/1995 | Phelps et al. . |
| 5,451,235 | 9/1995 | Lock et al. . |
| 5,456,693 | 10/1995 | Conston et al. . |
| 5,466,242 | 11/1995 | Mori . |
| 5,496,277 | 3/1996 | Termin et al. . |
| 5,522,822 | 6/1996 | Phelps et al. . |
| 5,527,338 | 6/1996 | Purdy . |
| 5,597,378 | 1/1997 | Jervis ........................................ 606/78 |
| 5,634,936 | 6/1997 | Linden et al. .......................... 606/213 |
| 5,645,558 | 7/1997 | Horton ..................................... 606/91 |
| 5,702,421 | 12/1997 | Schneidt ................................. 606/213 |
| 5,709,707 | 1/1998 | Lock et al. .............................. 606/213 |
| 5,733,294 | 3/1998 | Forber et al. ........................... 606/151 |

OTHER PUBLICATIONS

Duprat, Jr., et al. "Self–expanding Metallic Stents for Small Vessels: An Experimental Study", Radiology 1987; 162; 469–472.

Dotter, et al., "Transluminal Expandable Nitinol Coil Scent Grafting: Preliminary Report", Radiology 147; 259–260, 4/83.

Schatz, et al., "Balloon–expandable intracoronary stents in the adult dog", Circulation, vol. 76, No. 2, 8/87; 450–457.

Swenden Now, "When hope is all in vein", 1988.

Dotter, "Transluminally–placed Coilspring Endaterial Tube grafts, Long–term Patency in Canine Popliteal Artery", Investigative Radiology, vol. 4, Sep.–Oct., 1969; 329–332.

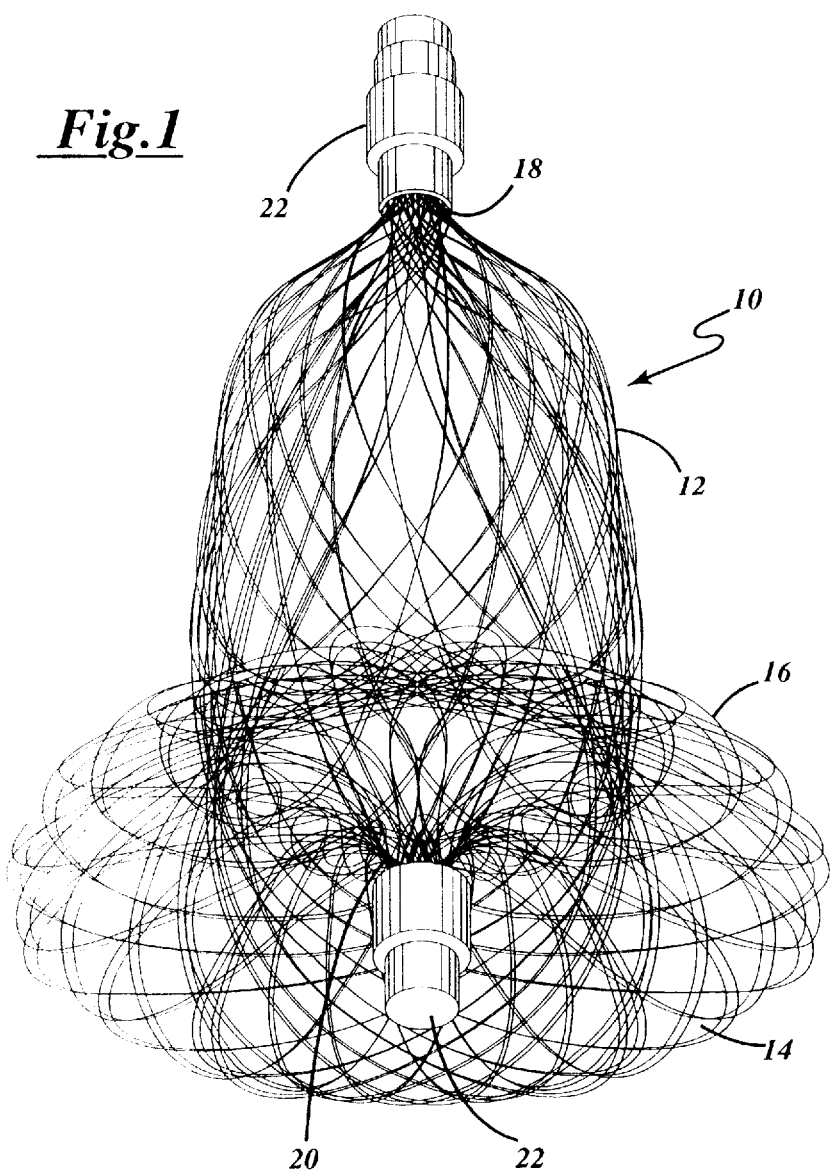

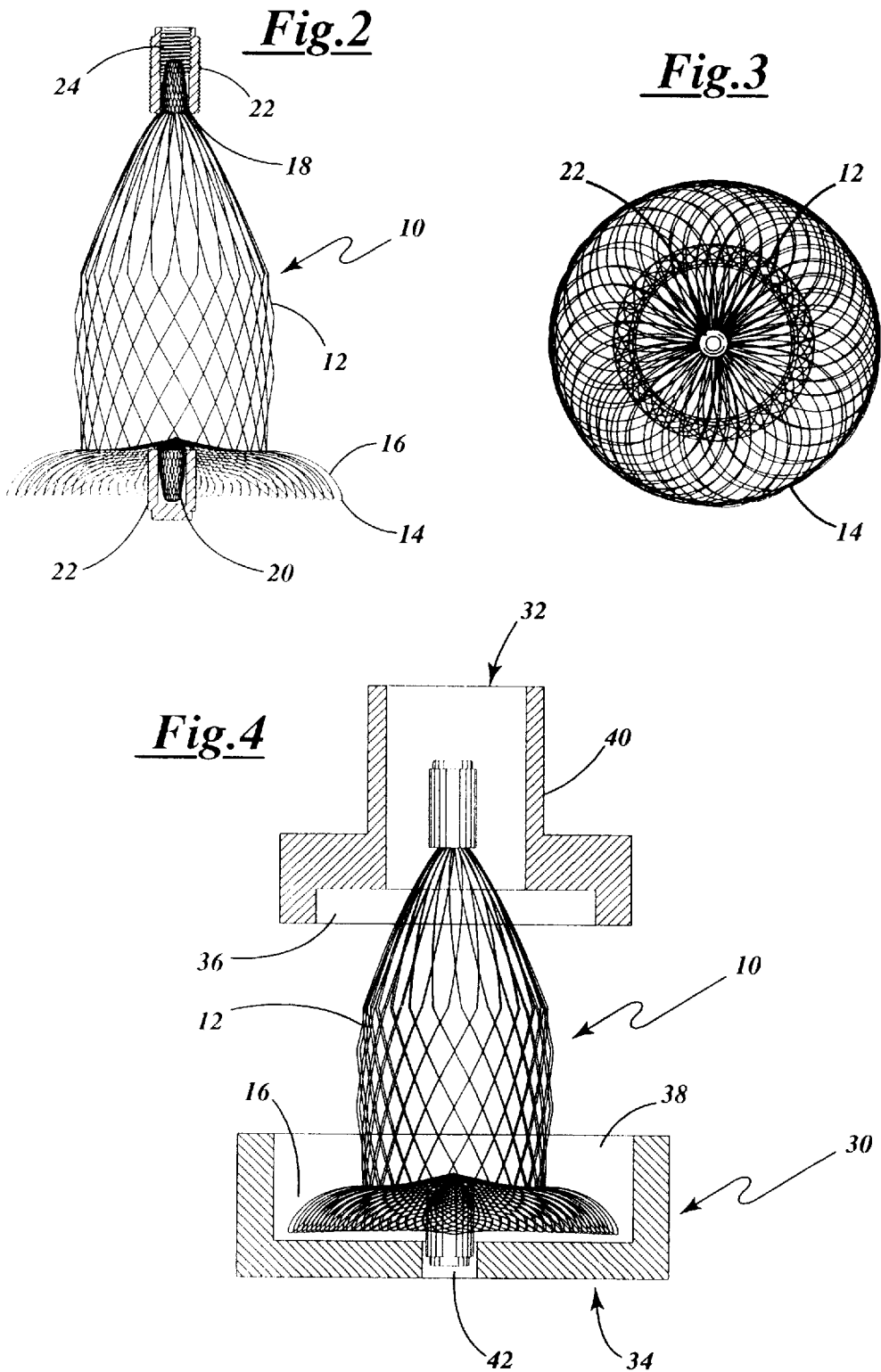

*Fig.19*
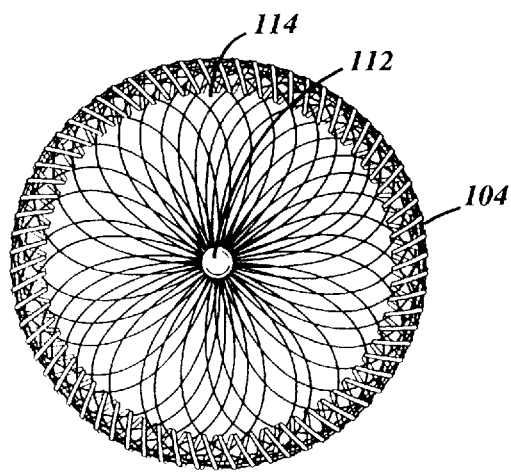
*Fig.20*
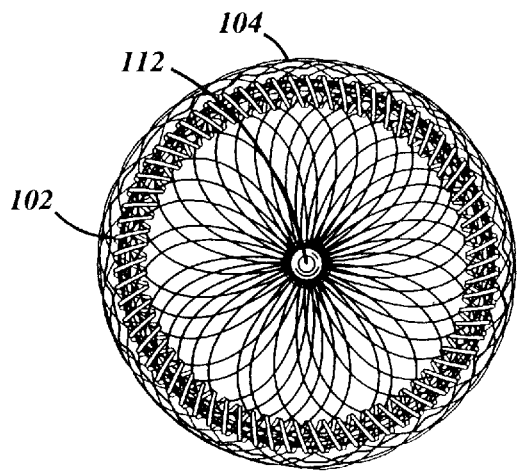
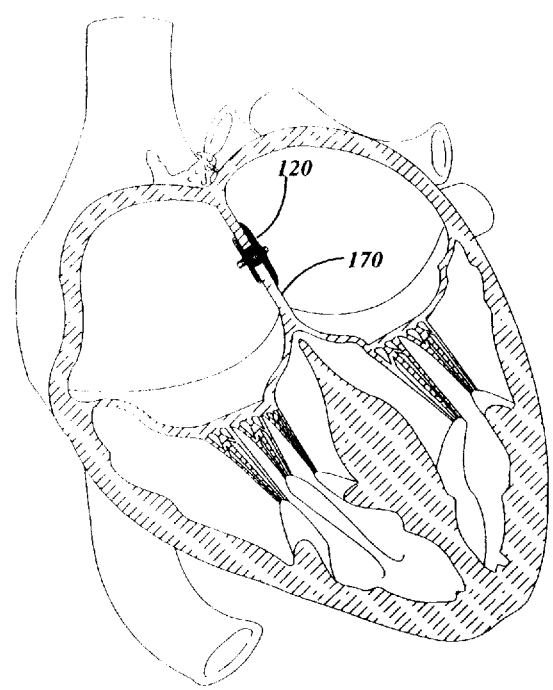
*Fig.21*

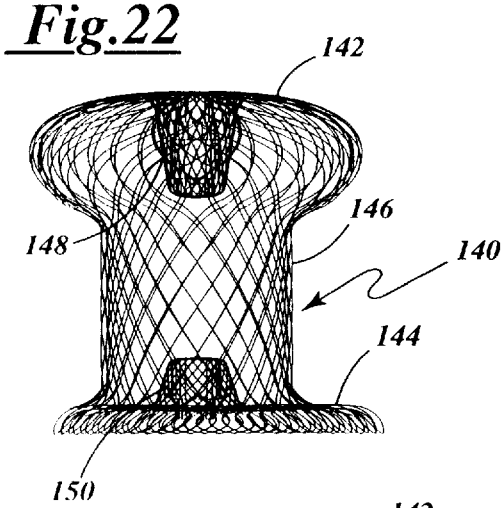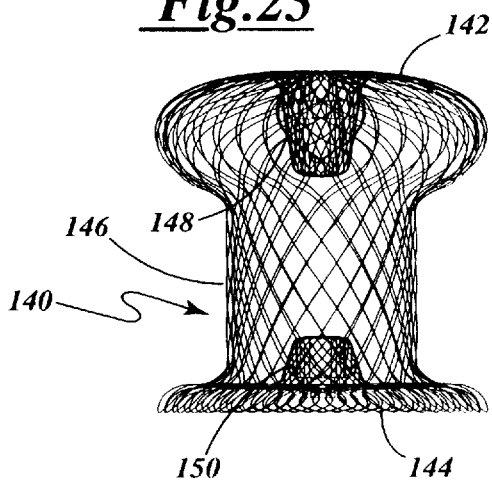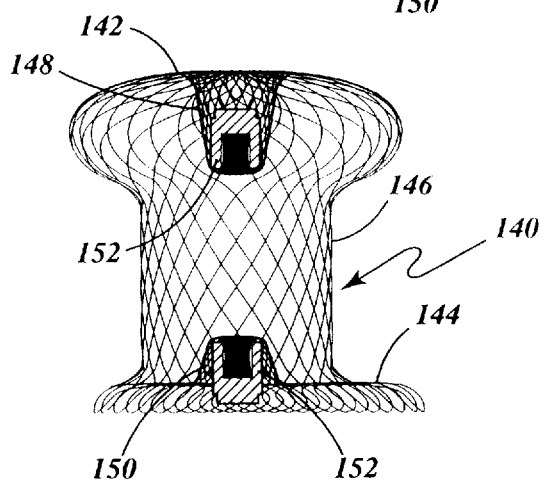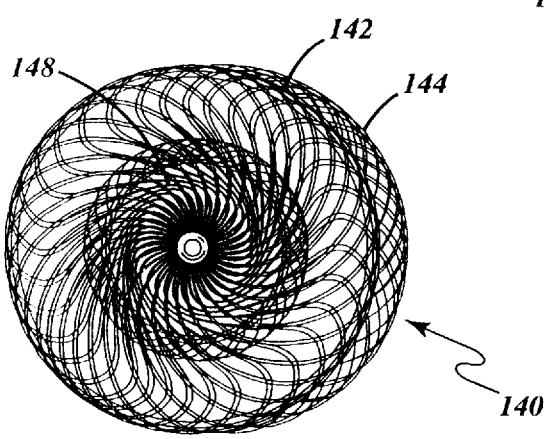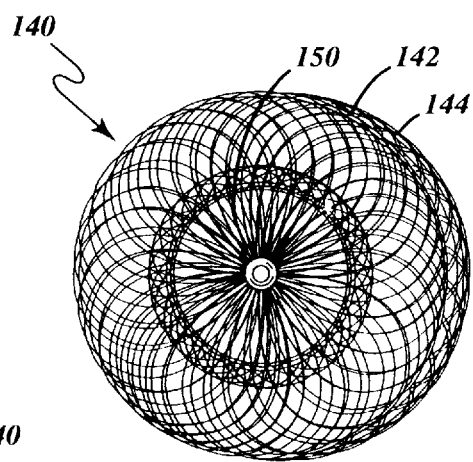

PERCUTANEOUS CATHETER DIRECTED OCCLUSION DEVICES

The present application is a Continuation-In-Part of application Ser. No. 08/647,712 filed on May 14, 1996, now U.S. Pat. No. 5,725,552 and entitled PERCUTANEOUS CATHETER DIRECTED INTRAVASCULAR OCCLUSION DEVICE which is a Continuation-In-Part of co-pending application Ser. No. 08/272,335, filed on Jul. 8, 1994, still pending and entitled "METHOD OF FORMING MEDICAL DEVICES; INTRAVASCULAR OCCLUSION DEVICES".

BACKGROUND OF THE INVENTION

I. Field of the Invention

The present invention generally relates to intravascular devices for treating certain medical conditions and, more particularly, relates to a low profile intravascular occlusion devices for treating congenital defects including Atrial and Ventricular Septal Defects (ASD and VSD respectively) and Patent Ductus Arteriosus (PDA). The devices made in accordance with the invention are particularly well suited for delivery through a catheter or the like to a remote location in a patient's heart or in analogous vessels or organs within a patient's body.

II. Description of the Related Art

A wide variety of intra cardiac devices are used in various medical procedures. For example, certain intravascular devices, such as catheters and guide wires, are generally used simply to deliver fluids or other medical devices to specific locations within a patient's heart, such as a selective coronary artery within the vascular system. Other, frequently more complex, devices are used in treating specific conditions, such as devices used in removing vascular occlusions or for treating septal defects and the like.

In certain circumstances, it may be necessary to occlude a patient's vessel, such as to stop blood flow through an artery to a tumor or other lesion. Presently, this is commonly accomplished simply by inserting, for example, Ivalon particles (a trade name for vascular occlusion particles) and short sections of coil springs into a vessel at a desired location. These "embolization agents" will eventually become lodged in the vessel, frequently floating downstream of the site at which they are released before blocking the vessel. This procedure is often limited in its utility, in part, due to the inability to precisely position the embolization agents. These embolization agents are not commonly used as an intra cardiac occluding device.

Balloon catheters similar to that disclosed by Landymore et al. in U.S. Pat. No. 4,836,204 have been used by physicians to temporarily occlude a septal defect until the patient stabilizes enough for open heart surgical techniques. When using such a catheter, an expandable balloon is carried on a distal end of a catheter. When the catheter is guided to the desired location, the balloon is filled with a fluid until it substantially fills the vessel and becomes lodged therein. Resins which will harden inside the balloon, such as an acrylonitrile, can be employed to permanently fix the size and shape of the balloon. The balloon can then be detached from the end of the catheter and left in place. If the balloon is not filled enough, it will not be firmly lodged in the septal defect and may rotate and loosen from the septal wall, thereby being released into the blood flowing from the right or left ventricular chamber. Overfilling the balloon is an equally undesirable occurrence which may lead to the rupture of the balloon and release of resins into the patient's bloodstream.

Mechanical embolization devices, filters and traps have been proposed in the past, representative examples of which are disclosed in King et al., U.S. Pat. No. 3,874,388 (the '388 patent), Das, U.S. Pat. No. 5,334,217 (the '217 patent), Sideris, U.S. Pat. No. 4,917,089 (the '089 patent) and Marks, U.S. Pat. No. 5,108,420 (the '420 patent). The '388, '217, '089, and '420 devices are typically pre-loaded into an introducer or delivery catheter and are not commonly loaded by the physician during the medical procedure. During deployment of these devices, recapture into the delivery catheter is difficult if not impossible, thereby limiting the effectiveness of these devices.

Significantly, the size of these devices is inherently limited by the structure and form of the device. When using occluding devices such as the '089, '388, '217, or '420 plug to occlude a septal defect, the pressure and therefore the chance of dislodgment of the device increases with the size of the defect. Consequently, these devices must have a very large retention skirt positioned on each side of the defect. Oftentimes, the position of the septal defect dictates the size of the retention skirt. In a membranous type septal defect, it is difficult if not improbable to be able to effectively position the '388, '217, '089, or '420 device without at least partially closing off the aorta. Also, these disclosed devices tend to be rather expensive and time-consuming to manufacture. Hence, it is desirable to provide a low profile device that is recoverable and retractable into the delivery system without increasing the overall thickness of the device which may be made with a relatively small retention skirt that is positionable within a membranous type septal defect without closing off the aorta.

Also, the shape of the prior devices (for example squares, triangles, pentagons, hexagons and octagons) require a larger contact area, having corners which extend to the free wall of the atria. Each time the atria contracts (approximately 100,000 times per day), internal wires within the prior art devices are bent creating structural fatigue fractures in approximately 30 percent of all cases. Furthermore, the previous devices require a French 14–16 introducing catheter, making it impossible to treat children affected with congenital defects with these devices.

Accordingly, it would be advantageous to provide a reliable embolization device which is both easy to deploy through a 6–7 French catheter and which can be accurately placed in a vessel or organ. It would also be desirable to provide a low-profile recoverable device for deployment in an organ of a patient's body.

SUMMARY OF THE INVENTION

It is accordingly a principal object of the present invention to provide a reliable, low-profile, intra cardiac occlusion device which may be formed to treat, for example, Ventricular Septal Defects (VSD), Atrial Septal Defects (hereinafter ASD), and Patent Ductus Arteriosus (hereinafter PDA). When forming these intravascular devices from a resilient metal fabric a plurality of resilient strands are provided, with the wires being formed by braiding to create a resilient material. This braided fabric is then deformed to generally conform to a molding surface of a molding element and the braided fabric is heat treated in contact with the surface of the molding element at an elevated temperature. The time and temperature of the heat treatment is selected to substantially set the braided fabric in its deformed state. After the heat treatment, the fabric is removed from contact with the molding element and will substantially retain its shape in the deformed state. The braided fabric so treated defines an expanded state of a medical device which can be deployed through a catheter into a channel in a patient's body.

Embodiments of the present invention provide specific shapes for medical devices which may be made in accordance with the present invention to address identified medical needs and procedures. The devices have an expanded low-profile configuration and may include recessed clamps that attach to an end of a delivery device or guide wire allowing recovery of the device after placement. In use, a guide catheter is positioned and advanced in a patient's body such that the distal end of the catheter is adjacent a desired treatment site for treating a physiological condition. A preselected medical device of the present invention having a predetermined shape is then collapsed and inserted into the lumen of the catheter. The device is urged through the catheter and out the distal end, whereupon, due to its memory property it will tend to substantially return to its expanded state adjacent the treatment site. The guide wire or delivery catheter is then released from the clamp and removed.

In accordance with a first of these embodiments, a generally elongate medical device has a generally tubular middle portion and a pair of expanded diameter portions, with one expanded diameter portion positioned at either end of the middle portion. The width of the middle portion approximates the wall thickness of the organ to be occluded, for example, the thickness dimension of the septum. The center of at least one of the expanded diameter portions may be offset relative to the center of the middle portion, thereby allowing occlusion of a membranous type ventricular septal defect while providing a retention skirt of sufficient size to securely close the abnormal opening in the septum. Each braided end of the device is held together with a clamp. The clamps are recessed into the expanded diameter portion of the device, thereby reducing the overall length dimension of the device and creating a low profile occluder.

In another embodiment, the medical device is generally bell-shaped, having an elongate body, a tapered first end, and a larger second end. The second end has a fabric disc which will be oriented generally perpendicular to an axis of a channel when deployed therein. The clamps which hold together the braided ends are recessed towards the center of the "bell" providing a low-profile device having a reduced overall height dimension.

BRIEF DESCRIPTION OF THE DRAWINGS

FIG. 1 is a perspective view of a medical device in accordance with the present invention;

FIG. 2 is a side view of the medical device of the type shown in FIG. 1;

FIG. 3 is a top view of the medical device of the type shown in FIG. 1;

FIG. 4 is a partial sectional side elevational view of a molding element suitable for forming the medical device shown in FIG. 1;

FIG. 19 is partial sectional top plan view of the ASD device of FIG. 17;

FIG. 20 is partial sectional bottom plan view of the ASD device of FIG. 17;

FIG. 21 is a partial sectional side elevational view of the ASD device of FIG. 17 shown positioned within an ASD of a patient's heart;

FIG. 22 is an enlarged, front elevational view of a medical device suitable for occluding a VSD shown in its pre-shaped configuration;

FIG. 23 is a side elevational view of the VSD device of FIG. 22;

FIG. 24 is a partial sectional front elevational view of the VSD device of FIG. 22;

FIG. 25 is a top plan view of the VSD device of FIG. 22;

FIG. 26 is a bottom plan view of the VSD device of FIG. 22;

DETAILED DESCRIPTION OF THE PREFERRED EMBODIMENTS

Figure 5:
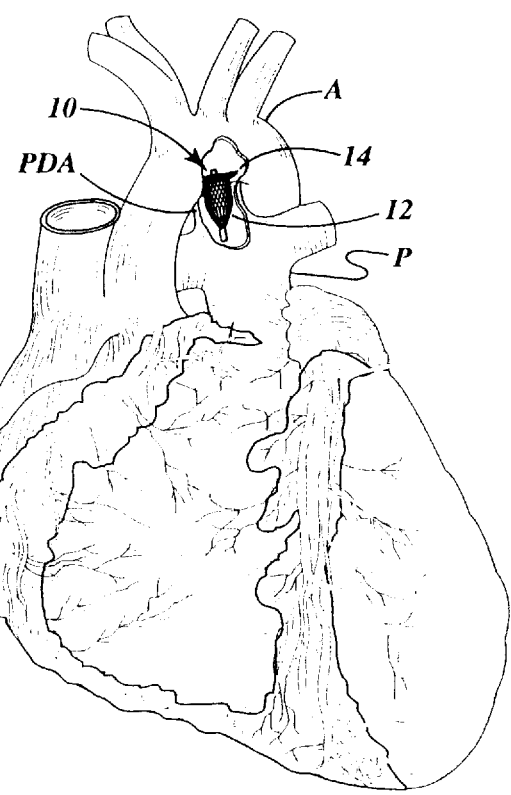
FIG. 5 is a partial sectional perspective view of a patient's heart showing the medical device of the type shown in FIG. 1 deployed in a central shunt of a patient's vascular system.
Figure 6:
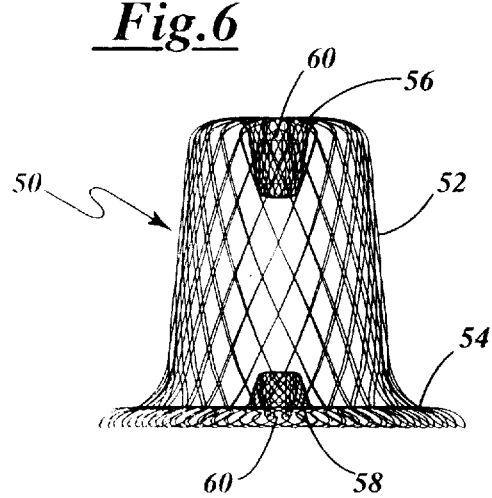
FIG. 6 is an enlarged, front elevational view of a medical device suitable for occluding a PDA.
Figure 7:
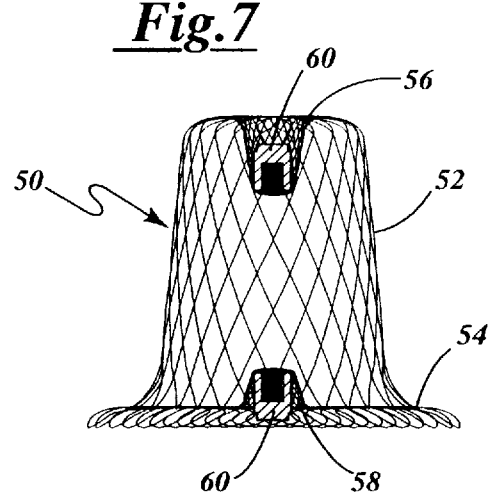
FIG. 7 is a partial sectional side elevational view of the PDA device of FIG. 6.
Figure 8:
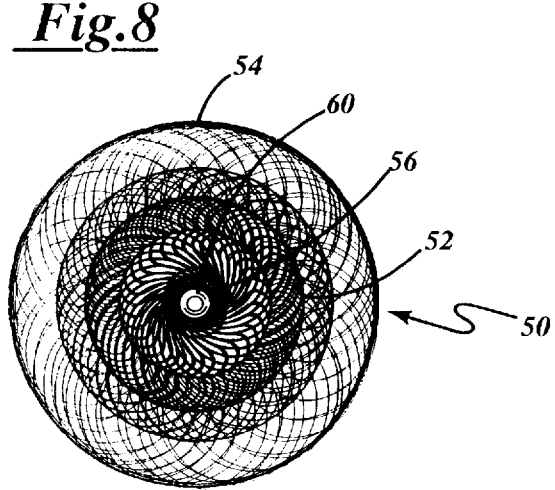
FIG. 8 is a top plan view of the PDA device of FIG. 6.
Figure 9:
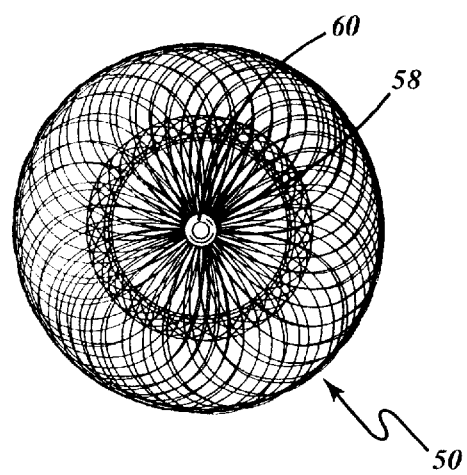
FIG. 9 is a bottom plan view of the PDA device of FIG. 6.

The present invention provides a percutaneous catheter directed occlusion device for use in occluding an abnormal opening in a patients' body, such as an Atrial Septal Defect (ASD), a ventricular septal defect (VSD), a Patent Ductus arteriosus (PDA), and the like. In forming a medical device via the method of the invention, a planar or tubular metal fabric is provided.

Both the planar and tubular fabrics are formed of a plurality of wire strands having a predetermined relative orientation between the strands. The tubular fabric has metal strands which define two sets of essentially parallel generally helical strands, with the strands of one set having a "hand", i.e. a direction of rotation, opposite that of the other set. This tubular fabric is known in the fabric industry as a tubular braid.

The pitch of the wire strands (i.e. the angle defined between the turns of the wire and the axis of the braid) and the pick of the fabric (i.e. the number of turns per unit length) as well as some other factors, such as the number of wires employed in a tubular braid, are important in determining a number of important properties of the device. For example, the greater the pick and pitch of the fabric, and hence the greater the density of the wire strands in the fabric, the stiffer the device will be. Having a greater wire density will also provide the device with a greater wire surface area, which will generally enhance the tendency of the device to occlude a blood vessel in which it is deployed. This thrombogenicity can be either enhanced by, e.g. a coating of a thrombolytic agent, or abated, e.g. by a coating of a lubricious, anti-thrombogenic compound. When using a tubular braid to form a device of the present invention, a tubular braid of about 4 mm in diameter with a pitch of about 50° and a pick of about 74 (per linear inch) would seem suitable for fabricating devices capable of occluding abnormal openings of about 2 mm to about 4 mm in inner diameter.

A metal planar fabric is a more conventional fabric and may take the form of a flat woven sheet, knitted sheet or the like. In the woven fabric there is typically two sets of generally metal strands, with one set of strands being oriented at an angle, e.g. generally perpendicular (having a pick of about 90°), with respect to the other set. As noted above, the pitch and pick of the fabric (or, in the case of a knit fabric, the pick and the pattern of the knit, e.g. Jersey or double knits) may be selected to optimize the desired properties of the resulting medical device.

The wire strands of the planar or tubular metal fabric are preferably manufactured from so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

Without any limitation intended, suitable wire strand materials may be selected from a group consisting of a cobalt-based low thermal expansion alloy referred to in the field as ELGELOY, nickel-based high temperature high-strength "superalloys" commercially available from Haynes International under the trade name HASTELLOY, nickel-based heat treatable alloys sold under the name INCOLOY by International Nickel, and a number of different grades of stainless steel. The important factor in choosing a suitable material for the wire strands is that the wires retain a suitable amount of the deformation induced by a molding surface (as described below) when subjected to a predetermined heat treatment.

In the preferred embodiment, the wire strands are made from a shape memory alloy, NiTi (known as nitinol) which is an approximately stoichiometric alloy of nickel and titanium and may also include other minor amounts of other metals to achieve desired properties. Handling requirements and variations of NiTi alloy composition are known in the art, and therefore such alloys need not be discussed in detail here. U.S. Pat. No. 5,067,489 (Lind) and U.S. Pat. No. 4,991,602 (Amplatz et al.), the teachings of which are incorporated herein by reference, discuss the use of shape memory NiTi alloys in guide wires. Such NiTi alloys are preferred, at least in part, because they are commercially available and more is known about handling such alloys than other known shape memory alloys. NiTi alloys are also very elastic and are said to be "super elastic" or "pseudo elastic". This elasticity allows a device of the invention to return to a preset expanded configuration for deployment.

When forming a medical device in accordance with the present invention, an appropriately sized piece of tubular or planar metal fabric is inserted into a mold, whereby the fabric deforms to generally conform to the shape of the cavities within the mold. The shape of the cavities are such that the metal fabric deforms into substantially the shape of the desired medical device. The ends of the wire strands of the tubular or planar metal fabric should be secured to prevent the metal fabric from unraveling. A clamp or welding, as further described below, may be used to secure the ends of the wire strands.

In the case of a tubular braid, a molding element may be positioned within the lumen of the braid prior to insertion into the mold to thereby further define the molding surface. If the ends of the tubular metal fabric have already been fixed by a clamp or welding, the molding element may be inserted into the lumen by manually moving the wire strands of the fabric apart and inserting the molding element into the lumen of the tubular fabric. By using such a molding element, the dimensions and shape of the finished medical device can be fairly accurately controlled and ensures that the fabric conforms to the mold cavity.

The molding element may be formed of a material selected to allow the molding element to be destroyed or removed from the interior of the metal fabric. For example, the molding element may be formed of a brittle or friable material. Once the material has been heat treated in contact with the mold cavities and molding element, the molding element can be broken into smaller pieces which can be readily removed from within the metal fabric. If this material is glass, for example, the molding element and the metal fabric can be struck against a hard surface, causing the glass to shatter. The glass shards can then be removed from the enclosure of the metal fabric.

Alternatively, the molding element can be formed of a material that can be chemically dissolved, or otherwise broken down, by a chemical agent which will not substantially adversely affect the properties of the metal wire strands. For example, the molding element can be formed of a temperature resistant plastic resin which is capable of being dissolved with a suitable organic solvent. In this instance, the fabric and the molding element can be subjected to a heat treatment to substantially set the shape of the fabric in conformance with the mold cavity and molding element, whereupon the molding element and the metal fabric can be emersed in the solvent. Once the molding element is substantially dissolved, the metal fabric can be removed from the solvent.

Care should be taken to ensure that the materials selected to form the molding element is capable of withstanding the heat treatment without losing its shape, at least until the shape of the fabric has been set. For example, the molding element could be formed of a material having a melting point above the temperature necessary to set the shape of the wire strands, but below the melting point of the metal forming the strands. The molding element and metal fabric can then be heat treated to set the shape of the metal fabric, whereupon the temperature can be increased to substantially completely melt the molding element, thereby removing the molding element from within the metal fabric. Those skilled in the art will appreciate that the shapes of the mold cavities and the molding elements may be varied in order to produce the medical device having a preselected size and shape.

It should be understood that the specific shape of a particular molding element produces a specific shape and other molding elements having different shape configurations may be used as desired. If a more complex shape is desired, the molding element and mold may have additional parts including a camming arrangement, but if a simpler shape is being formed, the mold may have few parts. The number of parts in a given mold and the shapes of those parts will be dictated almost entirely by the shape of the desired medical device to which the metal fabric will generally conform.

When the tubular braid for example is in its relaxed configuration, the wire strands forming the tubular braid will have a first predetermined relative orientation with respect to one another. As the tubular braid is compressed along its axis, the fabric will tend to flare out away from the axis conforming to the shape of the mold. When the fabric is so deformed the relative orientation of the wire strands of the metal fabric will change. When the mold is assembled, the metal fabric will generally conform to the molding surface of the cavity. The medical device has a preset expanded configuration and a collapsed configuration which allows the device to be passed through a catheter or other similar delivery device. The expanded configuration is generally defined by the shape of the fabric when it is deformed to generally to conform to the molding surface of the mold.

Once the tubular or planar metal fabric is properly positioned within a preselected mold with the metal fabric generally conforming to the molding surface of the cavities therein, the fabric can be subjected to a heat treatment while it remains in contact with the molding surface. Heat treating the metal fabric substantially sets the shapes of the wire strands in a reoriented relative position when the fabric conforms to the molding surface. When the metal fabric is removed from the mold, the fabric maintains the shape of the molding surfaces of the mold cavities to thereby define a medical device having a desired shape. This heat treatment will depend in large part upon the material of which the wire strands of the metal fabric are formed, but the time and temperature of the heat treatment should be selected to substantially set the fabric in its deformed state, i.e., wherein the wire strands are in their reoriented relative configuration and the fabric generally conforms to the molding surface.

After the heat treatment, the fabric is removed from contact with the molding element and will substantially retain its shape in a deformed state. If a molding element is used, this molding element can be removed as described above.

The time and temperature of the heat treatment can very greatly depending upon the material used in forming the wire strands. As noted above, one preferred class of materials for forming the wire strands are shape memory alloys, with nitinol, a nickel titanium alloy, being particularly preferred. If nitinol is used in making the wire strands of the fabric, the wire strands will tend to be very elastic when the metal is in its austenitic phase; this very elastic phase is frequently referred to as a super elastic or pseudo elastic phase. By heating the nitinol above a certain phase transition temperature, the crystal structure of the nitinol metal will tend to "set" the shape of the fabric and the relative configuration of the wire strands in the positions in which they are held during the heat treatment.

Suitable heat treatments of nitinol wire to set a desired shape are well known in the art. Spirally wound nitinol coils, for example, are used in a number of medical devices, such as in forming the coils commonly carried around distal links of guide wires. A wide body of knowledge exists for forming nitinol in such devices, so there is no need to go into great detail here on the parameters of a heat treatment for the nitinol fabric preferred for use in the present invention. Briefly, though, it has been found that holding a nitinol fabric at about 500 degrees centigrade to about 550 degrees centigrade for a period of about 1 to 30 minutes, depending upon the softness or hardness of the device to be made will tend to set the fabric in its deformed state, i.e., wherein it conforms to the molding surface of the mold cavities. At lower temperatures, the heat treatment time will tend to be greater (e.g., about 1 hour at about 350 degrees centigrade) and at higher temperatures the time will tend to be shorter (e.g., about 30 seconds at about 900 degrees centigrade). These parameters can be varied as necessary to accommodate variations in the exact composition of the nitinol, prior heat treatment of the nitinol, the desired properties of the nitinol in the finished article, and other factors which will be well known to those skilled in this field.

Instead of relying on convection heating or the like, it is also known in the art to apply an electrical current to the nitinol to heat it. In the present invention, this can be accomplished by, for example, connecting electrodes to each end of the metal fabric. The wire can then be heated by resistance heating of the wires in order to achieve the desired heat treatment, which will tend to eliminate the need to heat the entire mold to the desired heat treating temperature in order to heat the metal fabric to the desired temperature. The materials, molding elements and methods of molding a medical device from a tubular or planar metal fabric is further described in co-pending U.S. patent application Ser. No. 08/647,712, filed May 14, 1996 and assigned to the same assignee as the present invention, the entire disclosure of which is incorporated herein by reference.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment cite, such as immediately adjacent (or even within) the shunt of an abnormal opening in the patient's organ for example.

The delivery device (not shown) can take any suitable shape, but desirably comprises an elongate flexible metal shaft having a threaded distal end. The delivery device can be used to urge the medical device through the lumen of a catheter for deployment in a channel of a patient's body. When the device is deployed out the distal end of the catheter, the device will still be retained by the delivery device. Once the medical device is properly positioned within the shunt of the abnormal opening, the shaft of the delivery device can be rotated about its axis to unscrew the medical device from the delivery means.

By keeping the medical device attached to the delivery means, the operator can retract the device for repositioning relative to the abnormal opening, if it is determined that the device is not properly positioned within the shunt. A threaded clamp attached to the medical device allows the operator to control the manner in which the medical device is deployed out the distal end of the catheter. When the device exits the catheter, it will tend to resiliently return to a preferred expanded shape which is set when the fabric is heat treated. When the device springs back into this shape, it may tend to act against the distal end of the catheter effectively urging itself forward beyond the end of the catheter. This spring action could conceivably result in improper positioning of the device if the location of the device within a channel is critical, such as where it is being positioned in a shunt between two vessels. Since the threaded clamp can enable the operator to maintain a hold on the device during deployment, the spring action of the device can be controlled by the operator to ensure proper positioning during deployment.

Figure 10:
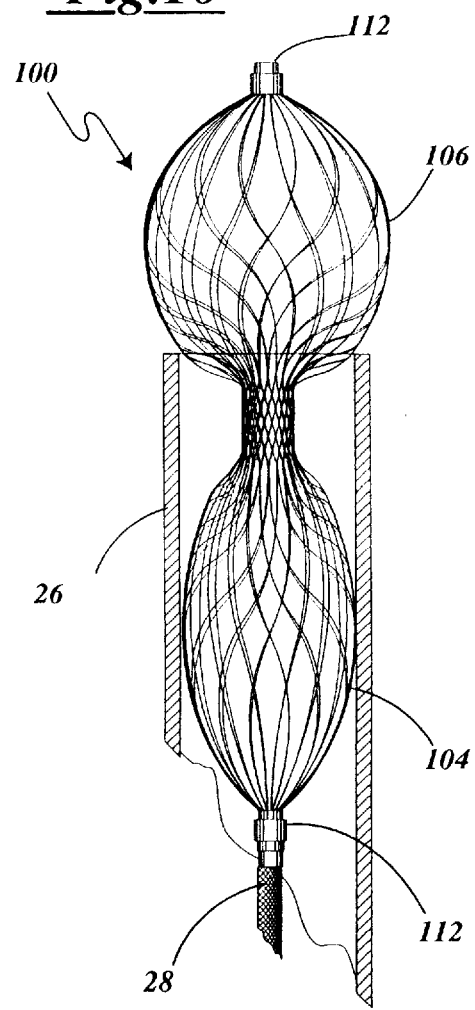
FIG. 10 is an enlarged, partial sectional view of a medical device suitable for occluding an ASD, shown stretched and partially extending out from the lumen of a delivery catheter.
Figure 11:
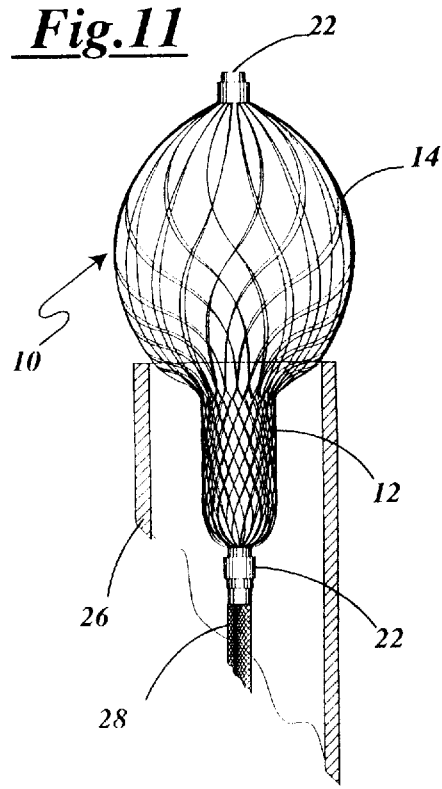
FIG. 11 is an enlarged, partial sectional view of a medical device suitable for occluding a PDA, shown stretched and partially extending out from the lumen of a delivery catheter.

The medical device can be collapsed into its collapsed configuration and inserted into the lumen of the catheter. The collapsed configuration of the device may be of any shape suitable for easy passage through the lumen of a catheter and proper deployment out the distal end of the catheter. For example, An ASD occluding device may have a relatively elongated collapsed configuration wherein the devices are stretched along their axes (see FIG. 10). This collapsed configuration can be achieved simply by stretching the device generally along its axis, e.g. by manually grasping the clamps and pulling them apart, which will tend to collapse the expanded diameter portions of the device inwardly toward the device's axis. A PDA occlusion device also operates in much the same fashion and can be collapsed into its collapsed configuration for insertion into the catheter by applying tension generally along the axis of the device (see FIG. 11). In this regard, these devices are not unlike "Chinese handcuffs", which tend to constrict in diameter under axial tension.

If the device is to be used to permanently occlude a channel in the patient's body, one can simply retract the catheter and remove it from the patient's body. This will leave the medical device deployed in the patient's vascular system so that it may occlude the blood vessel or other channel in the patient's body. In some circumstances, the medical device may be attached to a delivery system in such a manner as to secure the device to the end of the delivery means. Before removing the catheter in such a system, it may be necessary to detach the medical device from the delivery means before removing the catheter and the delivery means.

Although the device will tend to resiliently return to its initial expanded configuration (i.e. its shape prior to being collapsed for passage through the catheter), it should be understood that it may not always return entirely to that shape. For example, it may be desirable that the device have a maximum outer diameter in its expanded configuration at least as large as and preferably larger than, the inner diameter of the lumen of the abnormal opening in which it is to be deployed. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat the device therein.

When the device is deployed in a patient, thrombi will tend to collect on the surface of the wires. By having a greater wire density, the total surface area of the wires will be increased, increasing the thrombotic activity of the device and permitting it to relatively rapidly occlude the vessel in which it is deployed. It is believed that forming the occlusion device from a 4 mm diameter tubular braid having a pick of at least about 40 and a pitch of at least about 30° will provide sufficient surface area to substantially completely occlude an abnormal opening or blood vessel of 2 mm to about 4 mm in inner diameter in a suitable period of time. If it is desired to increase the rate at which the device occludes, any of a wide variety of known thrombotic agents can be applied to the device.

Referring now to the Figures, a discussion of the embodiments of the medical device of the present invention will next be presented. Referring first to FIGS. 1–3, there is shown generally a device 10 suitable for occluding a patent ductus arteriosus (PDA). PDA is essentially a condition wherein two blood vessels most commonly the aorta and the pulmonary artery adjacent the heart have a shunt between their lumens. Blood can flow directly between these two blood vessels through the shunt, compromising the normal flow of blood through the patient's vessels. The PDA device 10 has a generally bell-shaped body 12 and an outwardly extending forward end 14. The bell-shaped body 12 is adapted to be deployed within the shunt between the vessels while the forward end 14 is adapted to be positioned within the aorta to help seat the body of the device in the shunt. The sizes of the body 12 and the end 14 can be varied as desired for differently sized shunts. For example, the body 12 may have a diameter along its generally slender middle of about 10 mm and a length along its axis of about 25 mm. In such a device 10, the base of the body may flare generally radially outward until it reaches an outer diameter equal to that of the forward end 14 which may be on the order of about 20 mm in diameter.

The base 12 desirably flares out relatively rapidly to define a shoulder 16 tapering radially outwardly from the middle of the body 12. When the device 10 is deployed in a vessel, this shoulder 16 will abut the perimeter of the lumen being treated with higher pressure. The forward end 14 is retained within the vessel and urges the base of the body 12 open to ensure that the shoulder 16 engages the wall of the vessel to prevent the device from becoming dislodged from within the shunt.

A PDA occlusion device 10 of this embodiment of the invention can advantageously be made in accordance with the method outlined above, namely deforming a tubular metal fabric to generally conform to a molding surface of a mold and heat treating the fabric to substantially set the fabric in its deformed state. As noted above, the ends 18 and 20 of the tubular braid should be secured in order to prevent the braid from unraveling. In the preferred embodiment, clamps 22 are used to tie together the respective ends of the wire strands on each end 18 and 20 of the tubular braid. It is to be understood that other suitable fastening means may be attached to the ends in other ways, such as by welding, soldering, brazing, use of biocompatable cementious material or in any other suitable fashion. Each clamp 22 may include a threading 24 that serves to connect the device 10 to a delivery system (not shown). In the embodiment shown, the clamp 22 is generally cylindrical in shape and has a crimping recess for receiving the ends of the wire strands to substantially prevent the wires from moving relative to one another.

When using untreated NiTi fabrics, the strands will tend to return to their unbraided configuration and the braid can unravel fairly quickly unless the ends of the length of the braid cut to form the device are constrained relative to one another. The clamps 22 are useful to prevent the braid from unraveling at either end, thereby effectively defining an empty space within a sealed length of fabric. These clamps 22 hold the ends of the cut braid together and prevent the braid from unraveling. Although soldering and brazing of NiTi alloys has proven to be fairly difficult, the ends can be welded together, such as by spot welding with a laser welder. When cutting the fabric to the desired dimensions, care should be taken to ensure that the fabric will not unravel. In the case of tubular braids formed of NiTi alloys, for example, the individual strands will tend to return to their heat set configuration unless constrained. If the braid is heat treated to set the strands in the braided configuration, they will tend to remain in the braided form and only the ends will become frayed. However, it may be more economical to simply form the braid without heat treating the braid since the fabric will be heat treated again in forming the medical device.

FIG. 4 shows a mold 30 generally comprising an upper and lower plate 32 and 34 respectively. Corresponding cavities 36 and 38 are formed within each plate 32 and 34 to thereby define the molding surface of each upper and lower plate. The cavity 36 of the upper plate 32 is adapted to form the body portion 12 of the PDA device 10, while the lower plate's cavity 38 is adapted to form the shoulder 16 and forward end 14 of the PDA device 10. The upper plate 32 includes an elongate generally tubular central segment 40 which is sized to form the elongate body 12 of the PDA device 10. A portion of the upper plate's cavity 36 optimally has an internal diameter slightly less than the natural, relaxed outer diameter of the tubular braid of which the device is formed. The compression of the braid helps yield devices with reproducibly sized bodies 12. The bottom plate 34 of the mold 30 has a generally disk shaped cavity 38 which desirably has a clamp port 42 approximately centered therein for receiving the clamp 22 attached to one end of the tubular metal fabric.

In use, the metal fabric is placed within the cylindrical portion 40 of the cavity 36 of the upper plate 32. The upper and lower plates 32 and 34 are then brought together such that the cavity 38 of the bottom plate 34 engages the fabric and tends to urge the fabric under compression generally radially outward. The fabric will then be enclosed generally within the cavities 36 and 38 of the plates and will generally conform to the inner surface of the cavities. If one prevents the entire clamp 22 from passing through the clamp port 42, the fabric will be spaced slightly away from the inner surface of the face, yielding a slight dome shape in the forward end of the device. Although the illustrated embodiment includes such a dome shaped forward end 16, it is to be understood that the shoulder and forward end 14 may be substantially flat which can be accomplished by allowing the clamp 22 to be received entirely within the clamp port 42 in the end plate.

Once the fabric is compressed, the fabric can be subjected to a heat treatment such as is outlined above. When the mold 30 is open again by moving the upper and lower plates 32 and 34 away from one another, the fabric will generally retain its deformed, compressed configuration. The formed device 10 can be collapsed, such as by urging the clamps 22 generally axially away from one another, which will tend to collapse the device 10 toward its axis. The collapsed device can then be attached to a delivery device 28 and passed through a catheter 26 for deployment in a preselected site in the patient's body.

FIG. 5 schematically illustrates a PDA device 10 positioned in a patient's heart to occlude a PDA. The device 10 is shown positioned in a shunt, which extends between a patient's aorta "A" and the pulmonary artery "P". The device is passed through the PDA such as by keeping the device 10 collapsed within a catheter, and the shoulder 16 of the device can be allowed to elastically expand to substantially recover its thermally set, "remembered" shape from the heat treatment process, such as by urging the device distally to extend beyond the distal end of the catheter. The shoulder 16 should be larger than the lumen of the shunt of the PDA.

The device can then be retracted so that the shoulder 16 engages the wall of the pulmonary artery P. If one continues to retract the catheter, the engagement of the device 10 with the wall of the PDA will tend to naturally pull the body portion 12 of the device from the catheter, which will permit the body portion 12 to return to its expanded configuration. The body portion 12 should be sized so that it will frictionally engage the lumen of the PDA's shunt. The device will then be held in place by the combination of the friction between the body portion 12 and the lumen of the shunt and the aortic blood pressure against the shoulder 16 of the device. Over a relatively short period of time, thrombi will form in and on the device 10 and the thrombi will occlude the PDA. Those skilled in the art will appreciate that in order to speed up the occlusion of the device of the present invention, the device may be coated with a suitable thrombogenic agent, filled with a polyester fiber (see FIGS. 12–16), filled with a nylon sheet (see FIGS. 17–20) or braided with an increased number of wire strands.

Referring next to FIGS. 6–9, an alternative preferred PDA device 50 is shown. The device 50 includes a tapered cylindrical body portion 52 and a shoulder 54 extending radially outward from an end of the body portion. Each end 56 and 58 of the braided fabric is depressed inward towards the center of the lumen of the body portion 52. In this manner, clamps 60 attach to the ends of the tubular fabric are recessed within the device 50, thereby reducing the overall length of the PDA device and further creates a device lower in profile.

FIGS. 12–14 and 17–20 illustrates an alternate preferred embodiment of a medical device 100 in accordance with the present invention for correcting an atrial septal defect (ASD). With reference to FIGS. 12 and 17–20, the device 100 in its relaxed, unstretched state has two aligned disks 102 and 104 linked together by a short middle cylindrical section 106. It is proposed that this device 100 may also be well suited in occluding defects known in the art as patent foramen ovale (hereinafter PFO). Those skilled in the art will appreciate that a device of this configuration may also be suitable for use in a transcatheter closure during a Fenestrated Fontan's procedure. ASD is a congenital abnormality of the atrial septum characterized by structural deficiency of the atrial septum. A shunt may be present in the atrial septum, allowing flow between the right and left atriums. In large defects with significant left to right shunts through the defect, the right atrium and right ventricle are volume overloaded and the augmented volume is ejected into a low-resistance pulmonary vascular bed.

Pulmonary vascular occlusive disease and pulmonary atrial hypertension develops in adulthood. Patients with secundum ASD with a significant shunt (defined as a pulmonary blood flow to systemic blood flow ratio of greater than 1.5) are operated upon ideally at five years of age or whenever a diagnosis is made in later years. With the advent of two dimensional echocardiography and Doppler color flow mapping, the exact anatomy of the defect can be visualized. The size of the defect will correspond to the selected size of the ASD device 100 to be used.

The device 100, shown in its unconfined or relaxed state in FIGS. 12 and 17–20, is adapted to be deployed within the shunt comprising an ASD or a PFO (see FIG. 21). For exemplary purposes, use of the device 100 in an ASD closure procedure will be described below. Turning first to the constructional features of the device 100, the ASD occluder 100 is sized in proportion to the shunt to be occluded. In the relaxed orientation, the metal fabric is shaped such that two disk like members 102 and 104 are axially aligned and linked together by the short cylindrical segment 106. The length of the cylindrical segment 106 preferably approximates the thickness of the atrial septum, and ranges between 2 to 20 mm. The proximal 102 and distal 104 disks preferably have an outer diameter sufficiently larger than the shunt to prevent dislodging of the device. The proximal disk 102 has a relatively flat configuration, whereas the distal disk 104 is cupped towards the proximal end slightly overlapping the proximal disk 102. In this manner, the spring action of the device 100 will cause the perimeter edge 108 of the distal disk to fully engage the sidewall of the septum and likewise an outer edge of the proximal disk 102 will fully engage an opposite sidewall of the septum.

The ends of the tubular braided metal fabric device 100 are welded or clamped together with clamps 112, similar to those described above to avoid fraying. Of course the ends may alternately be held together by other means readily known to those skilled in the art. The clamp 112 tying together the wire strands at one end also serves to connect the device to a delivery system (see FIG. 10). In the embodiment shown, the clamp 112 is generally cylindrical in shape and has a recess for receiving the ends of the metal fabric to substantially prevent the wires comprising the woven fabric from moving relative to one another. The clamp 112 also has a threaded surface within the recess. The threaded recess is adapted to receive and engage a threaded distal end of a delivery device 28.

Figure 12:
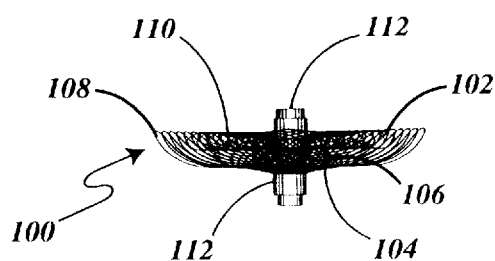
FIG. 12 is an enlarged front elevational view of an ASD device of the type shown in FIG. 10, shown in its pre-shaped configuration.
Figure 13:
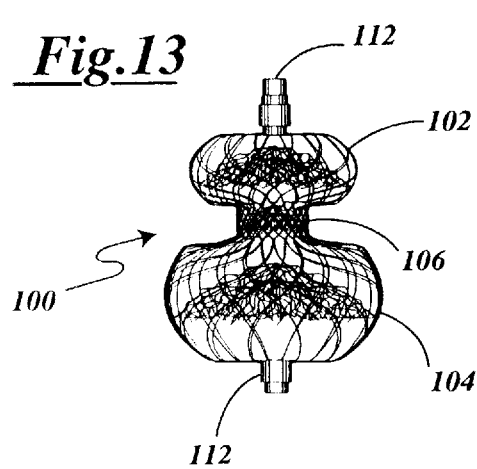
FIG. 13 is a side elevational view of the ASD device of FIG. 12, shown slightly stretched and filled with polyester fibers.
Figure 14:
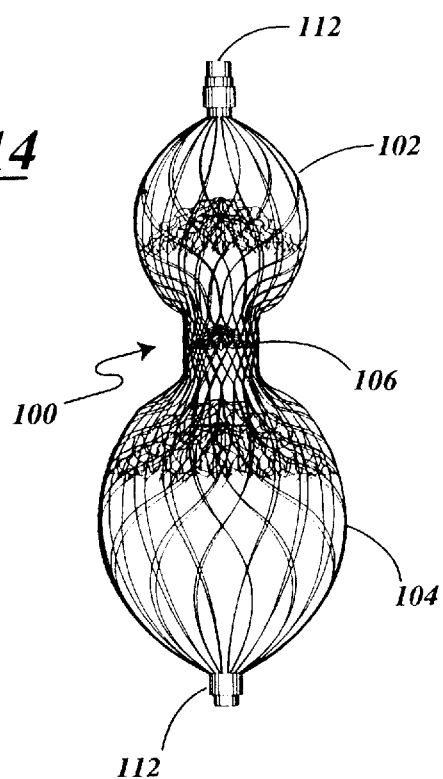
FIG. 14 is a side elevational view of the ASD device of FIG. 12, shown stretched and filled with polyester fibers.

The ASD occlusion device 100 of this embodiment of the invention can advantageously be made in accordance with the method outlined above. The device 100 is preferably made from a 0.005 inches nitinol wire mesh. The braiding of the wire mesh may be carried out with 28 picks per inch at a shield angle of about 64 degrees using a Maypole braider with 72 wire carriers. The stiffness of the ASD device 100 may be increased or decreased by altering the wire size, the shield angle, the pick size, the number of wire carriers or the heat treatment process. FIGS. 12–14 shows the interior lumen of the ASD device 100 filled with an occluding fiber of known suitable construction. FIGS. 17–20 shows the ASD device 100 having an occluding fabric 114 of known suitable construction contained within the interior of the device.

Figure 15:
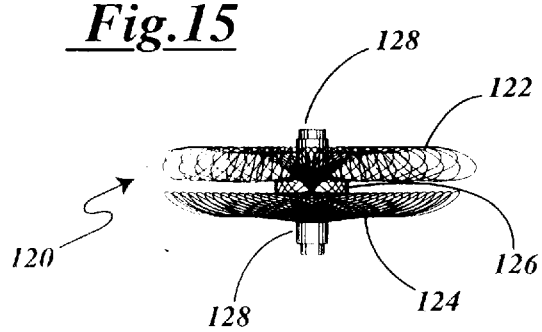
FIG. 15 is an enlarged front elevational view of an alternate ASD device, shown in its pre-shaped configuration.
Figure 16:
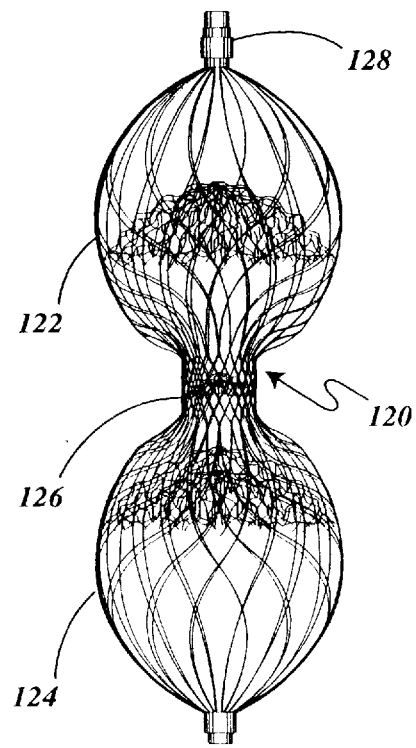
FIG. 16 is a side elevational view of the ASD device of FIG. 15, shown stretched and filled with polyester fibers.
Figure 17:
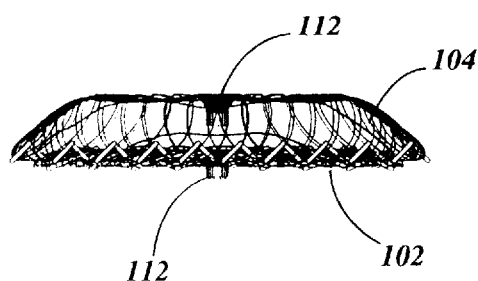
FIG. 17 is an enlarged front elevational view of another alternate ASD device, shown in its pre-shaped configuration.
Figure 18:
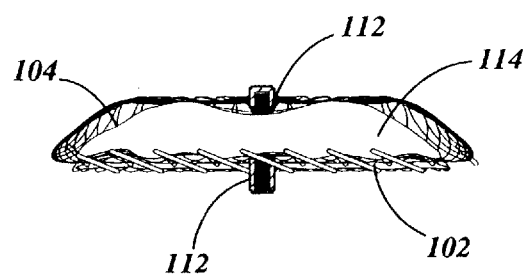
FIG. 18 is partial sectional side elevational view of the ASD device of FIG. 17.

Those skilled in the art will recognize from the preceding discussion that the cavities of a mold must be shaped consistent with the desired shape of the ASD device. Also, it will be recognized that certain desired configurations may require that portions of the cavities be cammed. FIGS. 15 and 16 illustrates an alternate ASD device 120 shown slightly stretched and having a modified configuration. The proximal disk 122 is a mirror image of distal disk 124, both of which are cup shaped. Each end is held by clamp 128. The distance separating the proximal and distal disks 122 and 124 is preferably equal or slightly less than the length of the cylindrical segment 126. The cup shape of each disk 122 and 124, ensures complete contact between the outer edge of each disk 122 and 124 and the atrial septum. Upon proper placement, a new endocardium layer of endothelial forms over the occlusion device 120, thereby reducing the chance of bacterial endocarditis.

The distance separating the disks 122 and 124 of occluding device 120 may be increased to thereby provide an occluding device suitable for use in occluding a channel within a patient's body, having particular advantages in use as a vascular occlusion device. The device 120 of FIGS. 15 and 16 includes a generally tubular middle portion 126 and a pair of expanded diameter portions 122 and 124. The expanded diameter portions are disposed at either end of the generally tubular middle portion. The relative sizes of the tubular middle section 126 and the expanded diameter portions 122–124 can be varied as desired. In this particular embodiment, the medical device is intended to be used as a vascular occlusion device to substantially stop the flow of blood through a patient's blood vessel. When the device 120 is deployed within a patient's blood vessel, it is positioned within the vessel such that its axis generally coincides with the axis of the vessel. The dumbbell shape is intended to limit the ability of the vascular occlusion device to turn at an angle with respect to the axis of the blood vessel to ensure that it remains in substantially the same position in which the operator deploys it within the vessel.

In order to relatively strongly engage the lumen of the blood vessel, the maximum diameter of the expanded diameter portions 122–124 should be selected so that it is at least as great as the diameter of the lumen of the vessel in which it is to be deployed and is optimally slightly greater than that diameter. When it is deployed within the patient's vessel, the vascular occlusion device will engage the lumen at two spaced apart locations. The device is desirably longer along its axis than the dimensions of its greatest diameter. This will substantially prevent the vascular occlusion device 120 from turning within the lumen at an angle to its axis, essentially preventing the device from becoming dislodged and tumbling along the vessel within the blood flowing through the vessel.

The relative sizes of the generally tubular middle portion 126 and expanded diameter portions 122–124 of the vascular occlusion device can be varied as desired for any particular application. For example, the outer diameter of the middle portion 126 may range between about ¼ and about ⅓ of the maximum diameter of the expanded diameter portions and the length of the middle portion 126 may comprise about 20% to about 50% of the overall length of the device 120. Although these dimensions are suitable if the device is to be used solely for occluding a vascular vessel, it is to be understood that these dimensions may be varied if the device is to be used in other applications, such as where the device is intended to be used simply as a vascular filter rather than to substantially occlude the entire vessel or where the device 120 is deployed to occlude an abnormal opening in an organ wall.

The aspect ratio (i.e., the ratio of the length of the device over its maximum diameter or width) of the device 120 illustrated in this embodiment is desirably at least about 1.0, with a range of about 1.0 to about 3.0 being preferred and then aspect ratio of about 2.0 being particularly preferred. Having a greater aspect ratio will tend to prevent the device 120 from rotating generally perpendicularly to its axis, which may be referred to as an end-over-end roll. So long as the outer diameter of the expanded diameter portions 122–124 of the device 120 is large enough to seat the device fairly securely against the lumen of the channel in which the device is deployed, the inability of the device to turn end-over-end will help keep the device deployed precisely where it is positioned within the patient's vascular system or in any other channel in the patient's body. Alternatively, having expanded diameter portions 122–124 which have natural relaxed diameters substantially larger than a lumen of the vessels in which the device is deployed should also suffice to wedge the device into place in the vessel without undue concern being placed on the aspect ratio of the device.

Turning now to FIGS. 22–26, a device 140 preferably suitable for occluding a membranous ventricular septal defect (VSD) is shown. The device 140 has an expanded preset configuration including two expanded diameter portions 142–144 and a reduced diameter portion 146 disposed between the two expanded diameter portions 142 and 144. Each of the expanded diameter portions 142 and 146 has a respective recess 148 and 150 extending inward from an outer surface of the expanded diameter portion 142 and 144. A clamp 152 attached to each end of the tubular metal fabric is contained within the corresponding recess 148–150 (see FIG. 24). The reduced diameter portion 146 has a length dimension which approximates a thickness of the abnormal opening formed in the septal wall. The expanded preset configuration of the device 140 is deformable to a lesser cross sectional dimension for delivery through a channel in a patient's body as described above. An inner surface of the expanded diameter portions may be concave or cupped (similar to that shown in FIGS. 15–16) to ensure that the outer perimeter of each diameter portion contacts the septal wall. Also, at least one of the expanded diameter portions 142 or 144 is offset relative to the reduced diameter portion 146. Thus, a center of one of the expanded diameter portion 142–144 will not align with the center of the reduced diameter portion 146. In this manner, when the abnormal opening is near the aorta, the offset retention skirt or expanded diameter portion 142–144 will not enclose the aorta upon placement.

Figure 27:
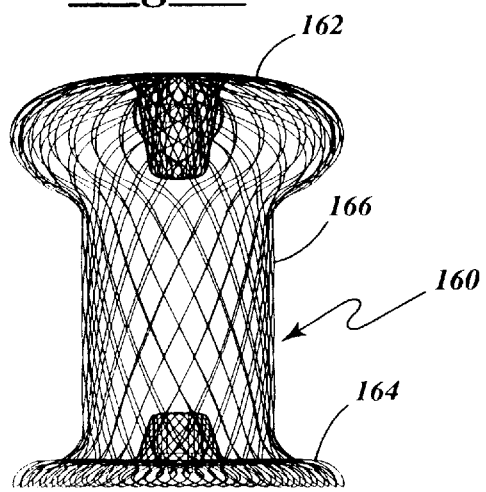
FIG. 27 is an enlarged front elevational view of an alternate VSD device, shown in its pre-shaped configuration.
Figure 28:
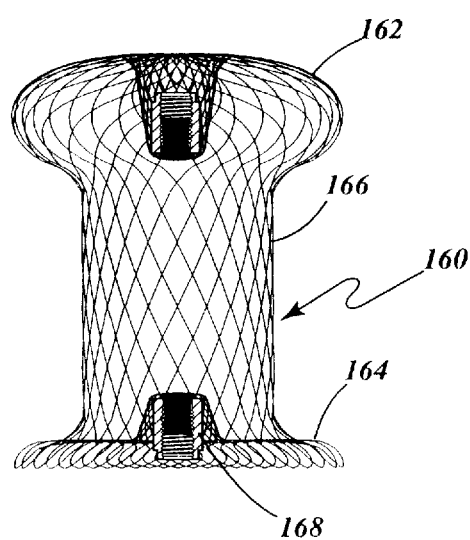
FIG. 28 is a partial sectional side elevational view of the VSD device of FIG. 27.

FIGS. 27 and 28 illustrate another alternate preferred VSD device 160 wherein the center of the both expanded diameter portions 162–164 and the reduced diameter portion 166 are aligned. Clamps 168 are attached to the ends of the metal fabric and are recessed inward to provide a low profile occluding device. The clamps 168 may have internal or external threading for attachment to a delivery device or guidewire. A device 160 of this shape is preferably used in occluding a muscular type ventricular septal defect. The delivery of the VSD device is similar to that described above.

Figure 29:
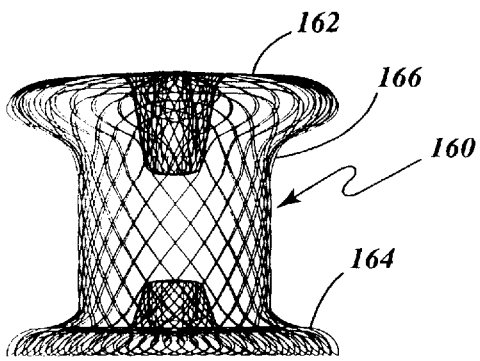
FIG. 29 is an enlarged front elevational view of an alternate VSD device, shown in its pre-shaped configuration.
Figure 30:
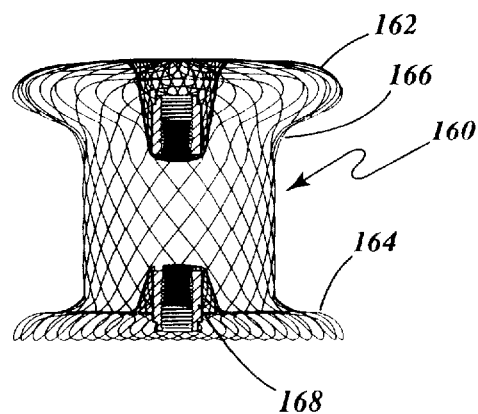
FIG. 30 is a partial sectional side elevational view of the VSD device of FIG. 29.
Figure 31:
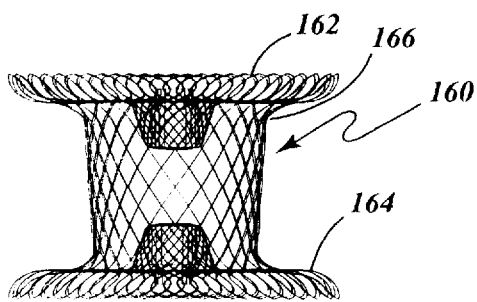
FIG. 31 is an enlarged front elevational view of an alternate VSD or PDA device, shown in its pre-shaped configuration.
Figure 32:
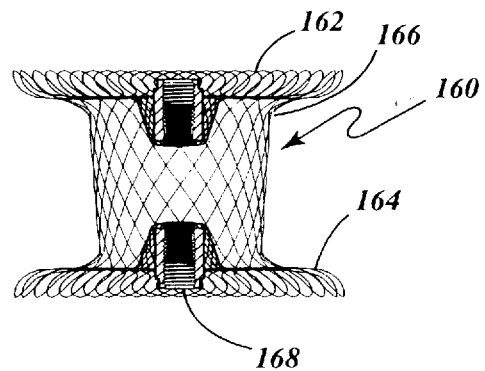
FIG. 32 is a partial sectional side elevational view of the VSD or PDA device of FIG. 31.

FIGS. 29 and 30 illustrate another embodiment of a device suitable for occluding a muscular VSD. The device of FIGS. 29 and 30 is similar to the VSD device shown in FIGS. 27 and 28 but includes modifications, wherein the length of the reduced diameter portion 166 is decreased and both expanded diameter portions 162–164 have been compressed thereby reducing the thickness dimension of each expanded diameter portion. FIGS. 31 and 32 illustrates another embodiment of a device similar to that shown in FIGS. 29 and 30. The device of FIGS. 31 and 32 is suitable for occluding a PDA, wherein the patient suffers from a pulmonary hyper tension. Both expanded diameter portions 162 and 164 are molded having a thin cross-section, to thereby avoid affecting the flow of fluid through the pulmonary vein or aorta. Further, the reduced diameter portion 166 is tapered to increase the surface area in contact with the tissue surrounding the defect.

Referring again to FIG. 21, the use of a device of the present invention will now be discussed in greater detail with respect to occluding a septal defect. The device 120, for example may be delivered and properly placed using two dimensional echocardiography and Doppler color flow mapping. As indicated above, the delivery device 28 can take any suitable shape, preferably comprising an elongated flexible metal shaft similar to a conventional guide wire. The delivery device 28 is used to advance the ASD occlusion device 120 through the lumen of a small diameter cylindrical tube 26, such as a delivery catheter, for deployment. The ASD device 120 is loaded into the small diameter cylindrical tube 26 by stretching the same to put it in an elongated condition. The device may be inserted into the lumen of the tube 26 during the procedure or preassembled at a manufacturing facility, in that the devices of the present invention do not take on a permanent set when maintained in a compressed state.

From a femoral vein approach, the delivery catheter or tube 26 is passed across the ASD. The device 120 is advanced through the delivery catheter until the distal end becomes unconstrained on exiting the end of the catheter, whereupon it assumes its disk-like shape in the left atrium. The delivery catheter 26 is then pulled back in the proximal direction across the ASD and the delivery device 28 is likewise pulled in a proximal direction, urging the distal disk against the septum 170. The delivery catheter 26 is then further pulled away from the septum 170, allowing the proximal disk to extend out of the delivery catheter 26, where it resiliently returns to its predefined expanded disk-like shape. In this manner, the ASD device 120 is positioned such that the distal disk presses against one side of the septum 170 while the proximal disk presses against the other side of the septum 170. In order to increase its occluding ability, the device can contain polyester fibers (see FIGS. 13 and 14) or a nylon fabric (see FIGS. 17–20). In instances where the device is improperly deployed on a first try, the device 120 may be recovered by pulling the delivery device 28 proximally, thereby retracting the device 120 back into the delivery catheter 26 prior to a second attempt at positioning the device 120 relative to the defect.

When the ASD occluding device 120 is properly placed, the physician rotates the delivery device 28, unscrewing the delivery device 28 from the clamp 128 of the occluding device 120. The threads on the clamp 128 are such that the rotation of the delivery device 28 unscrews the delivery device from the clamp 128 of the occluding device 120, rather than merely rotating the occluding device 120. As noted above in alternate embodiments, the threaded clamp can enable the operator to maintain a hold on the device during deployment, or enables the operator to control the spring action during deployment of the device to ensure proper positioning.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A collapsible medical device, comprising a metal fabric having an expanded preset configuration and including a recess in each of a proximal end and a distal end of the preset configuration, said proximal and distal end each having means for securing each end attached to the metal fabric and contained within the recess, wherein said medical device is shaped to create an occlusion of an abnormal opening, whereby said expanded preset configuration is deformable to a lesser cross-sectional dimension for delivery through a channel in a patient's body, the woven metal fabric having a memory property such that the medical device tends to return to said expanded preset configuration when unconstrained.

2. The medical device as recited in claim 1, wherein the expanded preset configuration comprises two expanded diameter portions and a reduced diameter portion disposed between the two expanded diameter portions, said reduced diameter portion having a length dimension which approximates a thickness of the abnormal opening.

3. The medical device as recited in claim 2, wherein an inner surface of at least one of the expanded diameter portions is concave.

4. The medical device as recited in claim 2, wherein an inner surface of a first expanded diameter portions is concave and a length of the reduced diameter portion is dimensioned such that a perimeter edge of the first expanded diameter portion overlaps a perimeter edge of a second diameter portion.

5. The medical device as recited in claim 2, wherein a center of at least one of the expanded diameter portions is offset relative to the center of the reduced diameter portion.

6. The medical device as recited in claim 1, wherein the reduced diameter portion has a length approximating a thickness of a patient's atrial septum.

7. The medical device as recited in claim 1, wherein the reduced diameter portion has a length approximating a thickness of a patient's ventricular septum.

8. The medical device as recited in claim 1, wherein said expanded preset configuration is in a shape of a bell.

9. The medical device as recited in claim 1, wherein said expanded preset configuration is in a shape of a dumbbell.

10. A collapsible medical device, comprising a metal fabric having an expanded preset configuration in a shape of a bell and including a recess in each of a proximal end and a distal end, said proximal and distal end each having means for securing each end attached to the metal fabric and contained within the recess, wherein said medical device is shaped to create an occlusion in a patent ductus arteriosus, whereby said expanded preset configuration is deformable to a lesser cross-sectional dimension for delivery through a channel in a patient's body, the woven metal fabric having a memory property such that the medical device tends to return to said expanded preset configuration when unconstrained.

11. A collapsible medical device, comprising a metal fabric having an expanded preset configuration including two expanded diameter portions and a reduced diameter portion disposed between the two expanded diameter portions, each expanded diameter portion having a recess extending inward from an outer surface of the expanded diameter portion, such that means for securing an outer edge of said metal fabric is attached thereto and contained within each recess, said medical device is shaped to create an occlusion of an abnormal opening and said reduced diameter portion has a length dimension which approximates a thickness of the abnormal opening, whereby said expanded preset configuration is deformable to a lesser cross-sectional dimension for delivery through a channel in a patient's body, the woven metal fabric having a memory property such that the medical device tends to return to said expanded preset configuration when unconstrained.

12. The medical device as recited in claim 11, wherein the reduced diameter portion has a length approximating a thickness of a patient's atrial septum.

13. The medical device as recited in claim 11, wherein the reduced diameter portion has a length approximating a thickness of a patient's ventricular septum.

14. The medical device as recited in claim 11, wherein an inner surface of at least one of the expanded diameter portions is concave.

15. The medical device as recited in claim 11, wherein an inner surface of a first expanded diameter portions is concave and a length of the reduced diameter portion is dimensioned such that a perimeter edge of the first expanded diameter portion overlaps a perimeter edge of a second diameter portion.

16. The medical device as recited in claim 11, wherein a center of at least one of the expanded diameter portions is offset relative to the center of the reduced diameter portion.

17. The medical device as recited in claim 11, wherein said means for securing includes an internal threading for attachment to a delivery device.

18. A collapsible medical device, comprising a metal fabric having an expanded preset configuration and having a proximal end and a distal end of the preset configuration, said proximal and distal end each having means for securing each end attached to the metal fabric, wherein the expanded preset configuration comprises two expanded diameter portions and a reduced diameter portion disposed between the two expanded diameter portions, said reduced diameter portion having a tapered cross-section extending between the two expanded diameter portions, whereby said expanded preset configuration is deformable to a lesser cross-sectional dimension for delivery through a channel in a patient's body, the woven metal fabric having a memory property such that the medical device tends to return to said expanded preset configuration when unconstrained.

\* \* \* \* \*